United States Patent
Flitsch et al.

(10) Patent No.: US 6,492,136 B1
(45) Date of Patent: Dec. 10, 2002

(54) SOLID PHASE ORGANIC SYNTHESIS

(75) Inventors: Sabine Lahja Flitsch; Nicholas John Turner, both of Edinburgh (GB)

(73) Assignee: Genzyme Limited, Suffolk (GB)

( * ) Notice: Subject to any disclaimer, the term of this patent is extended or adjusted under 35 U.S.C. 154(b) by 0 days.

(21) Appl. No.: 09/077,496

(22) PCT Filed: Dec. 6, 1996

(86) PCT No.: PCT/EP96/05535

§ 371 (c)(1),
(2), (4) Date: May 29, 1998

(87) PCT Pub. No.: WO97/20855

PCT Pub. Date: Jun. 12, 1997

(30) Foreign Application Priority Data

Dec. 7, 1995 (GB) ............................................ 95 25007
Jul. 3, 1996 (GB) ............................................ 96 13921

(51) Int. Cl.⁷ ........................ C12P 21/06; G01N 33/53; G01N 33/543; C07K 5/00; C07K 9/00
(52) U.S. Cl. ........................ 435/68.1; 435/7.1; 436/501; 436/518; 525/54.2; 530/300; 530/333; 530/334; 530/335; 530/322
(58) Field of Search ................................. 530/300, 333, 530/334, 335, 322; 525/54.2; 435/7.1, 68.1; 436/501, 518

(56) References Cited

U.S. PATENT DOCUMENTS 4,659,774 A * 4/1987 Webb et al. ................ 525/54.2
5,679,769 A * 10/1997 Danishefsky et al. ....... 530/322

OTHER PUBLICATIONS

Liang et al. "Parallel Synthesis and Screening . . . ", Science, vol. 274, pp. 1520–1522, Nov. 1996.*
Dineva et al. "Phenylacetyl Group as Enzyme–Cleavable . . . ", Bioorg. Med. Chem. Lett., vol. 3, No. 12, pp. 2781–2784, Dec. 1993.*

Hoffman, et al. "A New Safty–Catch Peptide–Resin Linkage For The Direct Release of Peptides into Aqueous Buffer," *Tetrahedron Letters*, 35: 7763–7766 (1994).
Hoffman, et al. "A Facile Preparation of N–(Isopropxyalkyl) Amides by Generation and Trapping of N–Acyliminium Ions from Ionization–Rearrangement Reactions of N–Triflyloxy Amides," *Journal of Organic Chemistry*, 59: 3530–3539 (1994).
Elmore, et al. "An Enzyme–scissile Linker for Solid–phase Peptide Synthesis," *J. Chem. Soc., Chem. Commun.*, 14: 1033–1034 (1992).

* cited by examiner

*Primary Examiner*—Jyothsna Venkat
*Assistant Examiner*—Maurie E. Garcia
(74) *Attorney, Agent, or Firm*—Jennifer Tegfeldt

(57) ABSTRACT

A method of synthesis of a material corresponding to the general formula:

$$R^3\text{—}X\text{—}H$$

characterized in that it comprises a material corresponding to the following general formula:

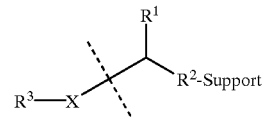

being cleaved as indicated enzymatically or non-enzymatically using acid catalysis in the presence of a nucleophile, wherein: $R^1$ represents a group providing the site for exo-enzyme or acid hydrolysis; $R_2$ represents an intermediate linked to a solid support; $R^3$ represents a carbohydrate, (oligo-)saccharide, (glyco-)peptide, (glyco-)lipid or an organic molecule which is at least one of heterocyclic and aromatic in structure; X represents O, N(H), N(R"), C(O)O, S, C(O)N(H) or C(O)N(R"), R" being a non-interfering group; and Support represents a solid support.

6 Claims, No Drawings

SOLID PHASE ORGANIC SYNTHESIS

This application claims the benefit of Great Britain Patent Application No. 95 25007.2, filed Dec. 7, 1995, and Great Britain Patent Application No. 96 13921.7 filed Jul. 3, 1996.

This invention relates to solid phase organic synthesis; more particularly, it relates to the use of certain linkers between reactant and support, which may be cleaved as desired by exo-enzymes.

As will be explained in more detail below, the present invention provides a method of synthesis of a material corresponding to the following general formula:

$$R^3—X—H$$

characterised in that it comprises a material corresponding to the following general formula:

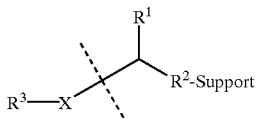

being cleaved as indicated enzymatically or non-enzymatically using acid catalysis in the presence of a nucleophile;
wherein $R^1$ represents a group providing the site for exo-enzyme or acid hydrolysis;

$R^2$ represents an optional intermediate linked to a solid support;

$R^3$ represents a residue of a carbohydrate, (oligo-) saccharide, (glyco-)peptide, (glyco-) lipid or of an organic molecule which is heterocyclic and/or aromatic;

X represents O, N(H), N(R"), C(O)O, S, C(O)N(H) or C(O)N(R"), R" being a non-interfering substituent; and Support represents a solid support.

Preferably $R^1$ represents: monosaccharide, phosphate, sulphate, —NH—CO—CH$_2$—Ph,

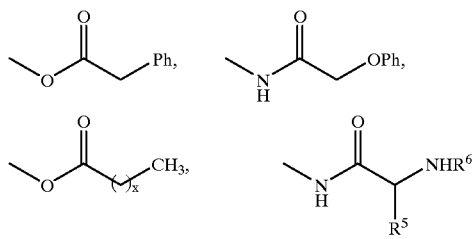

wherein x represents an integer; and $R^5$ and $R^6$ each represents a non-interfering group.

Preferably, $R^2$ represents:

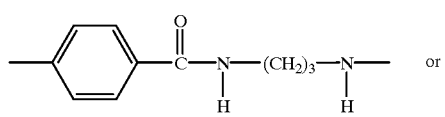

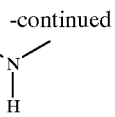

Preferably $R^3$ represents a residue of a (glyco-)peptide or (oligo-)saccharide.

Preferably, X represents O, N(H), N(R"), C(O)O, C(O)N (H) or S.

Preferably Support represents "EUPERGIT", amino-"TENTAGEL", "PEGA" resin or aminopropyl silica.

For the present purposes, the preferred exo-enzyme is penicillin amidase.

The present invention also relates to the use of an exo-linker in a solid phase organic synthesis.

The present invention further relates to a reagent corresponding to the formula:

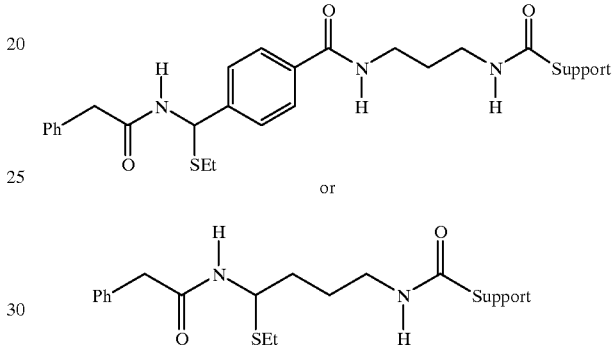

Having indicated the scope of the present invention, it will now be illustrated in more detail.

Solid phase organic synthesis is currently an area of great interest, particularly in the field of combinatorial synthesis. The anchoring of one component of a reaction to an insoluble support has the advantage that an excess of reagent may be used, while purification is kept manageable. This is particularly important if the reaction is to be carried out on a number of reactants in the same reaction vessel. Solid phase synthesis involves the use of linkers between the reactants and the solid supports which are stable during the reactions, but which may be cleaved as desired, usually at the end of the synthetic sequence, in high selectivity and yield, without affecting the structure(s) of the reactant(s) that are cleaved off the solid supports.

Linkers have previously been cleaved by chemical methods, in particular using strong acids.

Such conditions are not suitable for acid-labile compounds, such as carbohydrates. Specific linkers have therefore been developed for acid-labile compounds, such as silylether linkages (see, for example, Danishefsky, S. J., et al., Science, 260, 1307–1309, 1993), thioether linkages (see, for example, Kahne, D., et al., J. Am. Chem. Soc., 116, 6953–6954, 1994), and ester linkages (see, for example, Halcomb, R. L., et al., J. Am. Chem. Soc., 116 11315–11322, 1994; and Hindsgaul, O., et al., J. Chem. Soc., Chem. Commun., 1849, 1944). Although such linkers may be cleaved in the presence of acid-labile groups, they have the disadvantage that they are themselves quite labile to common chemical reagents that one might want to employ on the solid phase without affecting the linker. For example, esters and silylethers are unstable to base and thioethers are unstable in the presence of oxidants, such as m-chloroperbenzoic acid, and to electrophilic reagents, such as alkylating agents.

Enzymes would be particularly useful for such cleavage reactions because they may act catalytically under mild conditions and are highly selective in recognising specific substrate structures. Indeed, it has been shown that enzymes may be used for this purpose, (see, for example, Wong, C. H., et al., J. Am. Chem. Soc., 116, 1135, 1994), using a solid phase chemoenzymatic approach to the synthesis of glycopeptides, with the cleavage of a specific amide linker bond by α-chymotrypsin.

A current limitation of such an approach is that it requires the use of endo-enzymes, such as the endo-peptidase chymotrypsin, i.e. enzymes which cleave towards the middle of a chain or "internally". Not only does this limit the methodology to a very small number of enzymes, but it also restricts the structure of molecules that may be generated, e.g. the Wong method will always generate compounds containing C-terminal phenylalanine, which is necessary for recognition by chymotrypsin.

In order to overcome this problem, it is an object of the present invention to provide what are herein termed "exo-linkers" for use between reactants and solid supports. Such linkers do not restrict reactant structure and may be cleaved as desired by more readily available exo-enzymes, which act at the end of a chain or "externally".

According to the present invention, a linker is provided which has the effect of inserting an additional terminal group between the reactant and the support at the location of the previously-used endo-enzyme active site. The present invention is based on the insight that exo-enzyme action will result in hydrolysis without unavoidably retaining any enzyme recognition structure, thus allowing choice and control as regards the terminal function of the attached molecule.

An exo-linker according to the present invention may be illustrated as follows:

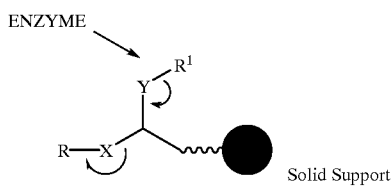

Solid Support

In this example, the reactant which is immobilized is R—XH. As will be appreciated by those skilled in the art, the nature of the moiety R may vary widely, but this type of methodology is often applied to glycopeptide, carbohydrate or oligosaccharide synthesis, for example. Typically, X may represent —O, —NH, —NR" (wherein R" represents a non-interfering substituent), —CO—O—, —CO—NH— or —S, for example. Commonly, Y represents —O or —NH, for instance. The structure of $R^1$ depends upon the choice of enzyme to be used in the cleavage reaction. For example, a range of hydrolytic exo-enzymes is available to cleave the Y—$R^1$ bond. By way of further illustration, there may be mentioned the following:

| $R^1$ | Enzyme |
|---|---|
| ![O=C-CH2-Ph] | Penicillin amidase |
| ![O=C-CH2-OPh] | SEM acylase |
| -monosaccharide | Glycosidase |
| -phosphate | Phosphatase |
| sulphate | Sulphatase |
| ![O=C-(CH2)x-CH3] | Esterase |
| ![O=C-CH(R)-NHR'] | Peptidase |

(Penicillin amidase is also known as penicillin aminohydrolase, EC 3.5.1.11.)

What distinguishes the present invention is that the bond to be cleaved by the enzyme is not part of the chain between the solid support and the material of interest, the reactant (R—X), but rather forms the "exo-linkage" between Y and $R^1$. A wide range of enzymes is known to those skilled in the art which would rely on recognizing only Y—$R^1$ and not the remainder of the structure. Once Y—$R^1$ is cleaved, the linkage between R—X and the support is very susceptible to generally concerted, acid-catalysed hydrolysis. Of course, this may involve more than simple hydrolysis as, say, methanol might be present, or it may form part of a coupling reaction, e.g. trans-acylation.

This type of approach is particularly suitable for the synthesis of complex molecules, such as glycopeptides, glycolipids, peptides and oligosaccharides, as well as derivatives thereof. The application of such methodology to, in particular, oligosaccharides and sugar derivatives facilitates the formation of libraries of derivatives in a combinatorial system, as will be appreciated by those skilled in the art. For example, well-developed selective chemistry is available for forming sugar derivatives by additions at hydroxyl functions, such as alkylation, esterification or sulfation/sulphonation, which may involve protection/deprotection chemistry. The presence of the sugar "scaffold" on a solid support allows the separation of reactants and products by simple filtration, for example. By the use of mixtures of derivatising compounds, e.g. using alkyl groups with variations in structure, a combination of compounds may be formed in each reaction cycle. It is known that such an approach may provide libraries of thousands of compounds. Such libraries are conventionally utilised in screens for discovering drug molecules. Such systems may be screened while attached to the solid phase, but preferably following exo-enzyme cleavage of the target molecules without potentially-interfering linker and solid phase in a single reaction under aqueous conditions suitable for incorporation into the assay without further chemistry and allowing appropriate adjustment of conditions, such as concentration.

It is readily apparent that, by the use of, for example, natural sugars, unnatural sugars, azido sugars or peptide sugar combinations and a variety of derivatising conditions, a wide range of both small and large changes may be made to the presentation of molecules in space. Carbohydrates may be mentioned as particularly advantageous in this approach as the high density of available hydroxyl groups leads to many potential connecting permutations, pyranose or furanose rings providing rigidity as homochiral building blocks. The availability of different stereoisomers, e.g. glucose, mannose, galactose, xylose, lactose, maltose and cellobiose, allows the exploration of changes in spatial orientation of functional groups, in addition to permutations achieved with oligosaccharides joined via different glycosidic linkages.

It is known that sugars may act as a "scaffold" to obtain non-peptidomimetics as has been demonstrated with a substance known as p partial agonist (see, for example, J. Am. Chem. Soc., 114, 9214–9218, 1992).

Carbohydrates are well known to be important in many biological systems, such as cell recognition and adhesion, and are already present in existing drugs, such as cardiac glycosides (e.g. digoxin), macrolide antibiotics (e.g. amikacin) and anti-cancer agents (e.g. doxorubicin).

In addition to allowing the formation of combinatorial libraries of compounds, the present exo-enzyme cleavable linker approach may also facilitate the synthesis of selected active molecules for further testing, additional analogue synthesis and use as therapeutic compounds or in the preparation thereof.

In the development of the present invention, it was first established that penicillin amidase is able to cleave phenylacetic acid from a solid support. Referring to illustrative Scheme 1 below, a model compound 1 was synthesised, was reduced to compound 2 and was coupled to derivatised aminopropyl silica, (see, for example, Matteucci, M. D., and Carruthers, M. H., J. Am. Chem. Soc., 103, 3185–3191, 1981), to give compound 3. Phenylacetic acid was indeed released from the solid support by the action of penicillin amidase in phosphate buffer, which indicates the potential for this enzyme in solid phase chemistry.

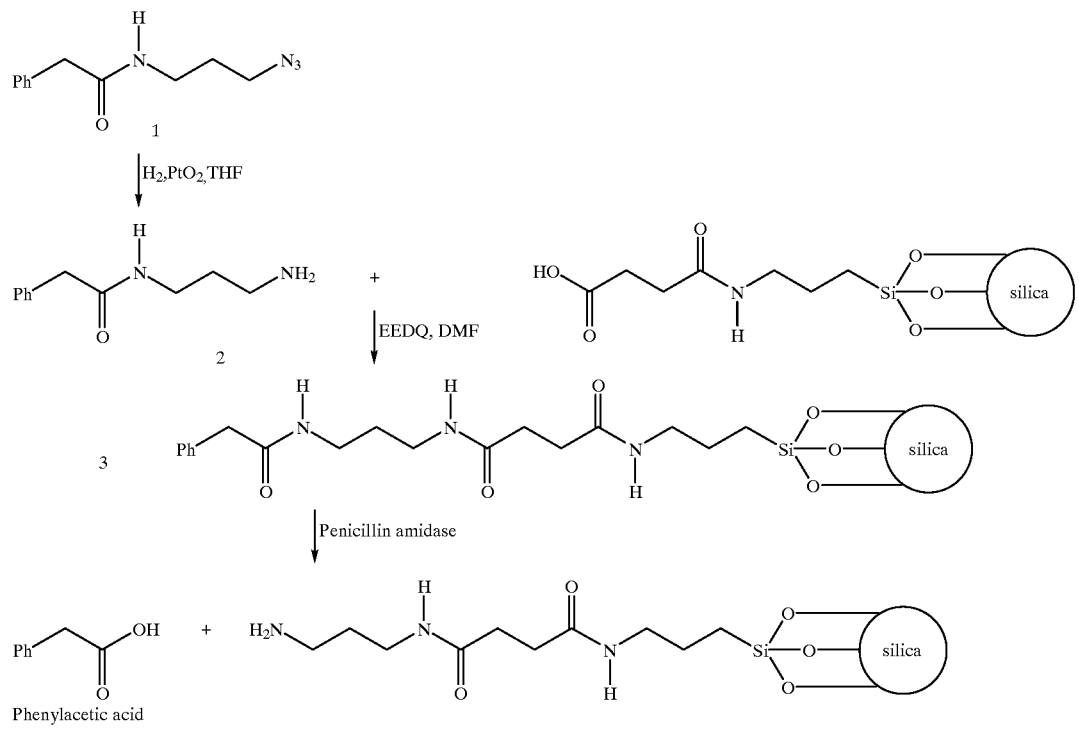

Scheme 1

By way of further illustration using the same enzyme, a soluble form of the present exo-linker 4 was hydrolysed by penicillin amidase to give the expected three products, viz glucose, phenylacetic acid and 4-carboxy-benzaldehyde, (ammonia release was not monitored). The exo-linker included in a soluble carbohydrate carrier exemplifying the enzyme hydrolysis of this complex molecule and unnatural substrate for penicillin amidase. See illustrative Scheme 2 below. It may be noted that the non-enzymatic hydrolysis of 4, which may be effected under acidic conditions, gives phenylacetamide rather than phenylacetic acid, thus indicating that the reaction shown below is indeed enzyme-catalysed and the enzyme-catalysed hydrolysis still occurs despite the presence of unnatural substituents as would be present in the solid phase form.

Scheme 2

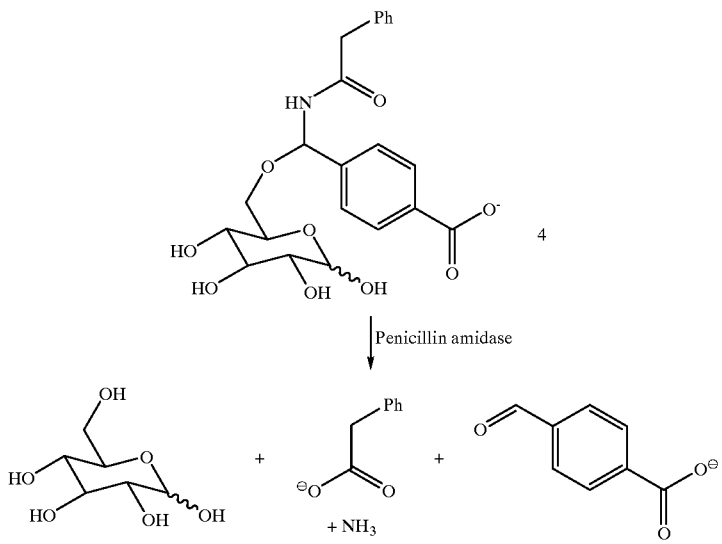

With reference to illustrative Scheme 3 below, the present enzyme-cleavable exo-linkers may be synthesised, for example, from suitably-substituted benzaldehydes, such as 5 and 6. Upon reflux with phenylacetamide and benzotriazole in toluene, the benzotriazole derivatives 7 and 8 were formed in this instance, (see, for example, Katritzky, A. R., et al, J. Chem. Soc., Perkin Trans. 1, 2339–2344, 1988; and Katritzky, A. R., et al, Heterocyclic Chem., 30, 381–387, 1993). Such benzotriazoles may be substituted by good nucleophiles, such as sodium ethyl thiolate, to generate the thioamidals 9 and 10, respectively. The thioether may be displaced by weaker nucleophiles in the presence of thiophilic reagents, such as N-iodosuccinimide (NIS), to lead to a variety of structures (11 & 12) in good yield. Direct displacement of the benzotriazole group in 7 and 8 with the weaker nucleophiles did not give these compounds (11 & 12) in an acceptable yield.

The $R^1$ group may be further modified after the coupling reaction. For example, the peracetylated glucosides 11 and 12 were deacetylated by treatment with triethylamine in methanol to give the glucosides 13 and 14. Further cleavage of the allylic ester of 13 lead to the free carboxylic acid 4.

The thioethyl group in 9 and 10 may also be easily displaced by amines, leading to 15 and 16. These compounds are equally susceptible to penicillin amidase hydrolysis, regenerating the corresponding amines $R^1H$.

Scheme 3

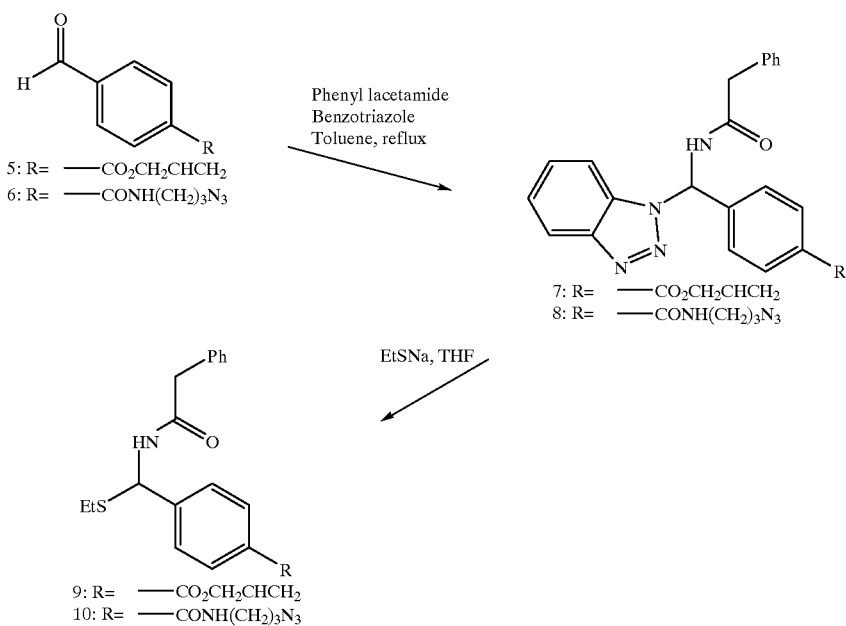

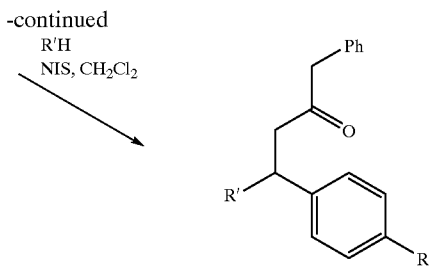

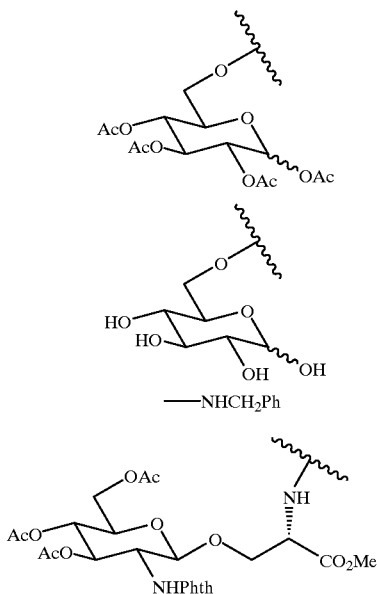

| | R | R¹ |
|---|---|---|
| 11 | —CO₂CH₂CH=CH₂ | |
| 12 | —CONH(CH₂)₃N₃ | |
| 13 | —CO₂CH₂CH=CH₂ | |
| 4 | —CO₂⁻ | |
| 14 | —CONH(CH₂)₃N₃ | |
| 15 | —CONH(CH₂)₃N₃ | —NHCH₂Ph |
| 16 | —CO₂CH₂CH=CH₂ | |

For example, compounds 4, 11–16 may be coupled to suitably functionalised resin, similarly to the method illustrated in Scheme 1 above, after deprotection of the carboxy or amino group of the R substituents. Thus, it has been demonstrated that the allyl ester may be cleaved using morpholine and Pd(PPh₃)₄ to give the free carboxylic acid. This may be coupled to resin containing free amino groups. Also, the azido group in compound 10, for example, may be reduced to an amino group, which would allow coupling to resin as outlined in Scheme 1.

Compound 10 and its amino analogue are both novel and are key intermediates in the present exo-cleavable solid phase system, providing a route for the synthesis of peptide, glycopeptide and sugar derivatives by displacement at the thioethyl group.

The present invention may be further illustrated by the following using penicillin amidase:

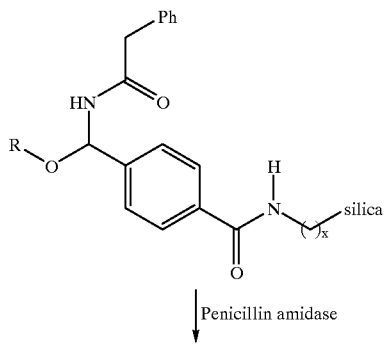

-continued

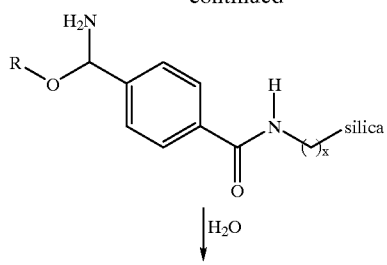

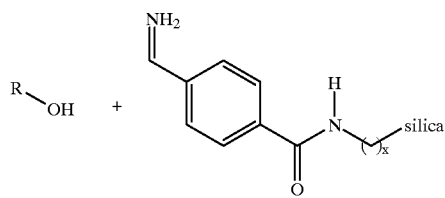

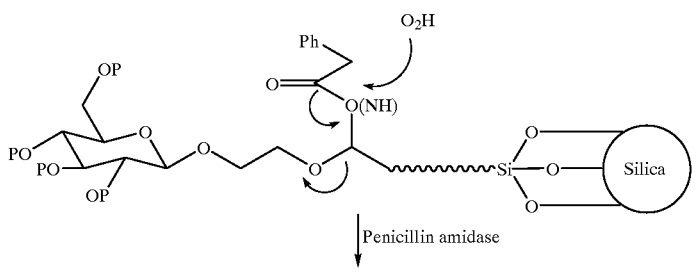

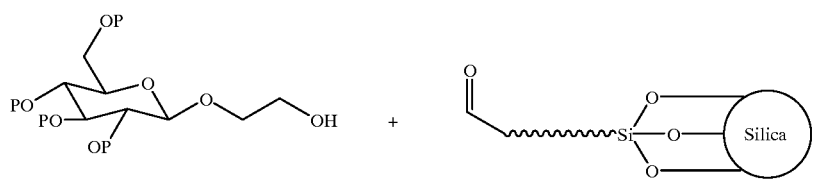

The potential solid supports for the present exo-linker methodology are not restricted to silica and may include various other known materials. By way of illustration, the azide compound 256 10 was reduced to amine and coupled to the commercially available "EUPERGIT" support, an oxirane acrylic resin available from Rohm & Haas, according to manufacturer's instructions. After coupling, the resin was washed thoroughly to remove unreacted amine. In order to demonstrate formation of the coupled product and the availability thereof to act as a substrate for an exo-enzyme, the coupled "EUPERGIT" support was treated with penicillin amidase. This released phenyl acetic acid, thus confirming that coupling had taken place and that release of the R moiety using an exo-enzyme was possible. The release of phenyl acetic acid was equivalent to 0.2 mmol/g of support. Chemical cleavage using 2M NaOH released phenyl acetic acid equivalent to 0.6 mmol/g of support. Such is further illustrated by the following scheme with the formation of compound 17 involving linker attached to solid "EUPERGIT" support.

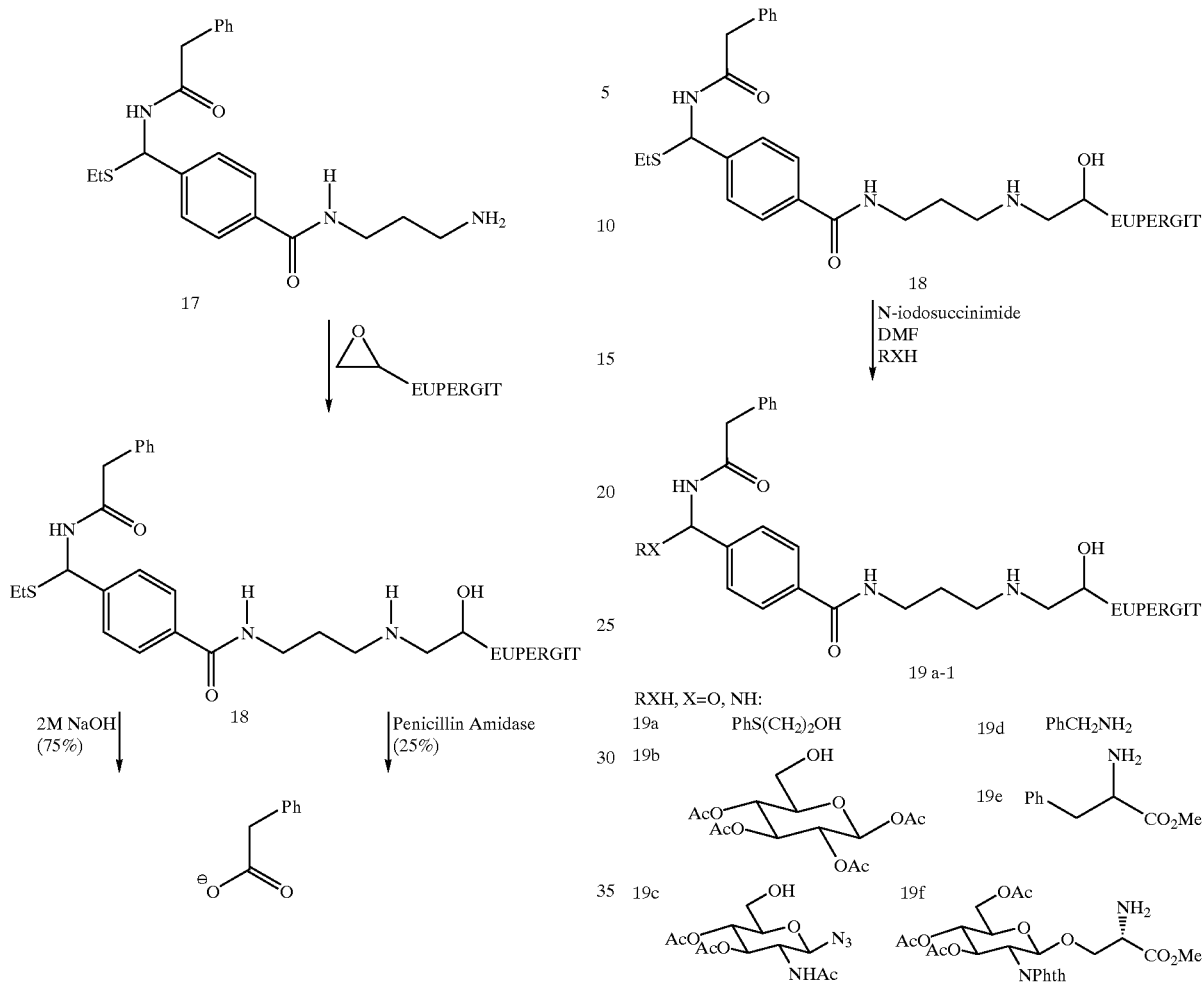

Other examples of suitable solid supports which have been used to attach linker 17 are as follows:

| Resin | Loading[1] (mmol/g resin) | Yield of cleavage[2] |
|---|---|---|
| TENTAGEL COOH (Advanced ChemTech) | 0.144 | 50% |
| TENTAGEL HL COOH (Rapp Polymere) | 0.240 | 11% |
| TENTAGLE MB COOH (Rapp Polymere) | 0.163 | 22% |
| PEGA COOH (Novabiochem) | 0.300 | 24% |

[1] Compound 17 was attached to the resin by reaction with TBTU/HOBt/DIEA (2 equivalents each). The loading was calculated after cleavage of the linker with NaOH and determinafion of the released phenylacetic acid.
[2] The resin-bound linker was treated with penicillin amidase and cleavage was calculated from the amount of phenylacetic acid released.

Compound 18 was demonstrated to be a versatile intermediate by the synthesis of compounds 19 a–f. Following activation of compound 12 with N-iodosuccinimide, a variety of alcohols and amines were coupled to give compounds 19 a–f which further illustrate the moieties exemplified as R' in compounds 11–16.

The reaction conditions for the formation of compounds 19 a–f were based on the following general procedure:

To a flask containing resin 18 (10 mg, 6.4 μmol linker) was added dry DMF (150 μl), followed by N-iodosuccinimide (2.9 mg, 12.8 μmol). The mixture was shaken for 2 minutes at room temperature and a solution of the alcohol or amine (2–10 mol eq. to linker) in dry DMF (100 μl) was added. The reaction mixture was then shaken (160 rpm, automated G24 environmental incubator shaker, New Brunswick Scientific) at 40° C. for a further 3.5 hours, diluted with water and the iodine removed by adding of a spatula of sodium thiosulphate. The resin was finally washed thoroughly with water, methanol and ether, then dried under vacuum.

The yield of this reaction was estimated from acid hydrolysis of resin 19a. Resin 19a (2 mg) was suspended in a 200 μl solution of different acids. The resulting components released from the resin were detected and quantified by HPLC. The loading of the resin was found to be identical to that of the starting material 18, indicating that 19a had been formed in near quantitative yield.

As an alternative to the use of an exo-enzyme, it has also been found that hydrolysis of the exo-linker may be accomplished under acidic conditions. Such an embodiment also forms part of the present invention. This alternative may be used when the alcohol or amine substituents (ROH or RNH$_2$) as illustrated in 19a and 19f are stable to acid. The same product results whether acidic hydrolysis or an exo-enzyme is used and thus these alternatives are interchangeable, substitution permitting.

The following Table shows the results obtained using compound 19a with a variety of acid conditions:

| Acid | Time | Phenylacetamide % | 2-phenyl-thioethanol % |
|---|---|---|---|
| 2 M HCl | 35 minutes | 100 | 100 |
| 0.2 M HCl | 35 minutes | 32 | 100 |
| | 2.5 hours | 64 | 100 |
| | 4.5 hours | 85 | 100 |
| 0.02 M HCl | 15 minutes | 24 | 20 |
| | 4 hours | 43 | 100 |
| 95% TFA | 45 minutes | 54 | 30 |
| | 2 hours | 85 | 24 |
| 20% TFA | 35 minutes | 80 | 92 |
| | 2.5 hours | 100 | 100 |
| 0.1 M TsOH | 30 minutes | 60 | 100 |

The release of phenylacetamide is consistent with acid hydrolysis as shown for compound 4 described earlier where enzymatic hydrolysis would yield phenylacetic acid and ammonia. The release of 2-phenyl-thioethanol indicates that acid catalysis releases the alcohol of interest from the linker. The results show that, by using an appropriate combination of pH, acid type and time, control may be achieved over hydrolysis of alcohol or amine preferentially over phenylacetamide resulting from the linker.

The mild acid conditions required for the cleavage from a solid support may even be used for some acid labile compounds, such as glycosylserine derivative 19f. Hydrolysis of 19f using 0.06M TsOH lead to release of 2-N-phthalimido-3,4,6-O-acetyl-β-D-glucopyranosyl-L-serine methyl ester. This compound was shown as a single peak by HPLC.

It is also possible to vary the structure of the linker molecule to form one having a non-aryl structure. The reaction sequence below illustrates the synthesis and hydrolysis using penicillin amidase of a non-aryl linker. The removal of the aryl moiety from the linker allows a reduction to 20% of the enzyme used previously. Such alternative linkers indicate that additional control is possible over reaction conditions, such as use of acid reaction conditions during solid phase chemistry.

Furthermore, the present invention may be applied to the chemoenzymatic synthesis of oligosaccharides, such as the illustrated synthesis of the disaccharide 24.

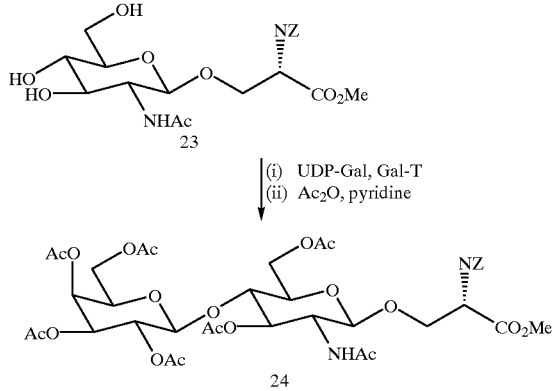

General—Reactions were carried out in solvents distilled from standard drying agents; TLC was performed on aluminium sheets coated with silica gel 60F$_{254}$ (Merck; layer thickness 0.2 mm); the components were revealed by UV detection; for the detection of sugar derivatives a solution of 5% sulfuric acid-5% anisaldehyde in ethanol was used; for the detection of amino derivatives a solution of 0.3% ninhydrin-3% acetic acid in butan-1-ol was used; silica gel C60 (Merck 40–60 μm) was used for flash chromatography, and Sorbsil C200 silica gel RP18 (40–60 μm, BDH) for reverse-phase chromatography; HPLC was carried out on a Spherisorb ODS (5 μm) column (4.6 mm internal diameter, 250 mm length) using two eluents (A-25 mM KPO$_4^{3-}$ pH=6.5; B-Acetonitrile); an automated Dionex system (flow=1 ml/min; run course=50 min.; gradient: t 32 0 min.—100% A and 0% B; t=0.1 min.—100% A and 0% B; from t=0.1 to 20 min.—0 up to 15% B; from t=20 to 40 min.—15 up to 70% B, from t=40 to 42 min.—70% B, from t=42 to 47 min.—70 up to 0% B, from t=47 to 50 min.—0% B and 100% A), and two UV detectors at λ=215 nm and λ=254 nm; NMR spectra were recorded on Varian Gemini 200 MHz, Bruker AM-500 MHz and 200 MHz spectrometers; mass spectrometry was carried out on BIO-Q mass spectrometers using ammonia desorption chemical ionisa-

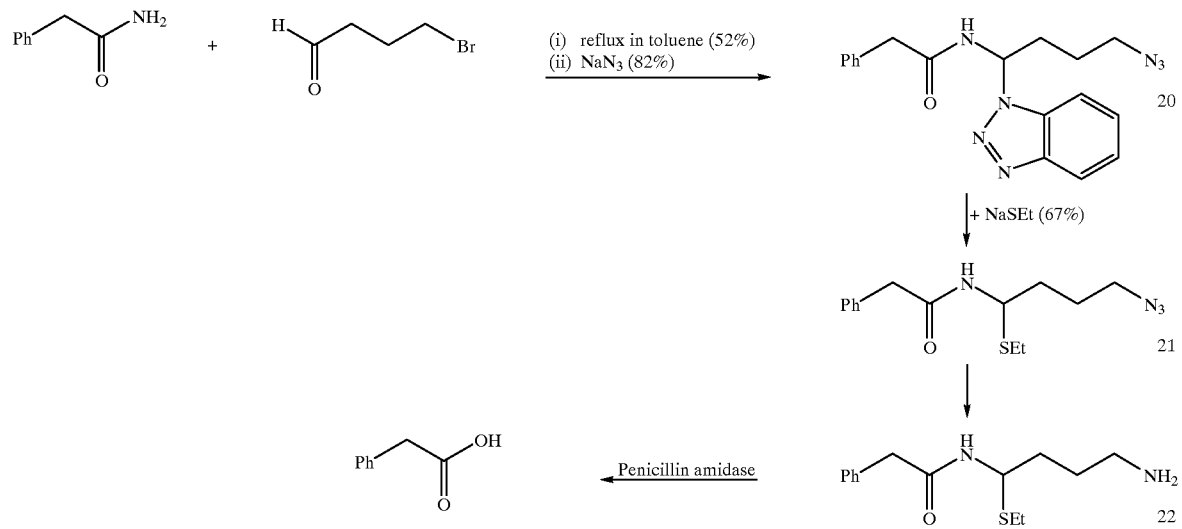

tion (DCI/NH$_3$), positive argon fast-atom bombardment (FAB) and electrospray (ES) as indicated; 1,2,3,4-tetra-O- acetyl-β-D-glucopyranose, penicillin amidase, "EUPERGIT" support and 3-aminopropyl silica gel were purchased from Sigma; N-iodosuccinimide, phenylacetyl chloride, 3-chloropropylamine hydrochloride and benzotriazole were purchased from Aldrich; 2-phenylacetamide was purchased from TCI; methanol HPLC Grade was purchased from Rathburn; water AnaiR was purchased from BDH; petroleum ether refers to the fraction in the range 40–60° C.; all enzymatic assays were performed using an automated pH stat unit (including a PHM82 standard pHmeter, a TTT80 Titrator with an electrode, a ABU80 Autoburette and a REC Servograph).

General procedure for enzymatic hydrolysis.—Penicillin amidase (221 μl, 250 units) was added carefully at room temperature to a solution of substrates (7.4 μmol) in 50 mM phosphate buffer pH=8 (1.5 ml). During the experiment, the pH was automatically maintained at pH8 by addition of an aqueous solution of 0.1 M sodium hydroxide. The reaction progress was followed by HPLC, where the retention times of the products were found to be identical to those of authentic materials.

N-azidopropyl phenylacetamide 1.—Phenylacetyl chloride (899 mg, 5.8 mmol) dissolved in diethylether (5 ml) was added dropwise at 0° C. to a solution of 1-azido 3-aminopropane, (see, for example, Carboni, B., et al, J. Org, Chem., 58, 3736–3741, 1933), (580 mg, 5.8 mmol) and triethylamine (972 μl, 6.96 mmol) in diethylether (10 ml). The reaction mixture was then stirred at room temperature for 1 hour and washed with a saturated solution of NaHCO, (25 ml). The aqueous layer was extracted with $CHCl_3$ (20 ml=2) and the organic layers combined, dried over sodium sulfate, filtered and concentrated under reduced pressure. The residue was chromatographed with ethyl acetate-petroleum ether (2:1) ($R_f$ 0.48) to give compound 1 as an oil (1.16 g, 92%); $v_{max}(CHCl_3)cm^{-1}$ 3400 (NH), 2980–2800 (CH), 2100 (—$N_3$), 1680 (CO), 1520 (C=$C_{ar}$); $δ_H$(200 MHz; $CDCl_3$) 1.75 (2H, m, $CH_2$—$CH_2N_3$), 3.3 (4H, m, $NHCH_2$ and $CH_2$ $N_3$), 3.6 (2H, s, $CH_2CO$), 5.65 (1H, s broad, NH), 7.3 (5H, m, Ph).

N-aminopropyl phenylacetamide 2.—A solution of N-azidopropyl-phenylacetamide 1(20 mg, 91.7 μmol) in dry THF (1 ml) was hydrogenated for 3 hours at room temperature under atmospheric pressure using $H_2$ in the presence of $PtO_2$ (5 mg) as a catalytic agent. The reaction progress was followed by UV detection and ninhydrin test. The reaction mixture was then filtered and concentrated under reduced pressure to give compound 2 as a colourless oil (16 mg, 90%); $δ_H$(200 MHz; $CDCl_3$) 1.60 (2H, m, $CH_2$—$CH_2NH_2$), 1.95 (2H, s, broad, $NH_2$), 2.7 (2H, t, J 7, $CH_2$ NH2), 3.3 (2H, m, $NHCH_2$), 3.55 (2H, s, $CH_2CO$), 6.25 (1H, s broad, NH), 7.3 (5H, m, Ph).

Coupling of compound 2 on solid support—Modified silica gel (50 mg), compound 2 (16 mg, 0.09 mmol) dissolved in DMF (0.5 ml) and EEDQ (26 mg, 0.1 mmol) were shaken under argon overnight at room temperature. The solid material was then washed with methanol (2 ml×3), diethylether (2 ml×3) and dried in vacuo at 65° C. for 3 hours.

Allyl-4-formylbenzoate 5.—A solution of 4-carboxy benzaldehyde (1 g, 6.66 mmol) in allyl alcohol (9 ml) was treated with $BF_3.Et_2O$ (1.64 ml, 13.32 mmol) and heated at 60° C. for 5 hours. Water (20 ml) was added and the mixture extracted with diethyl ether (70 ml×2). The organic layer was dried over sodium sulfate, filtered and concentrated under reduced pressure. The residue was chromatographed with petroleum ether-ethyl acetate (8:2) to give 5 as a white solid (686.3 mg, 54%): m.p. 35° C.; $R_f$ 0.34; $δ_H$(200 MHz; $CDCl_3$) 4.86–4.90 (2H, m, $OCH_2$), 5.32–5.50 (2H, m, $CH_2$=CH), 5.98–6.14 (1H, m, CH=$CH_2$), 7.98 (2H, d, J 8.40, $C_6H_4$), 8.25 (2H, d, J 8.40, $C_6H_4$), 10.13 (1H, s, CHO); $δ_C$(50 MHz; $CDCl_3$)66.09 ($OCH_2$), 118.92 (CH=$CH_2$), 129.65, 130.36 (4 CH, Ar), 131.90 (CH=$CH_2$), 135.21, 139.30 (2 C), 165.43 ($CO_2$), 191.96 (CHO); m/z (EI) Found: 190.0630 ($M^+$), $C_{11}H_{10}O_3$ requires 190.0630.

4-formyl-(N-azidopropyl)-benzamide 6.—Thionyl dichloride (650 μl, 8.9 mmol) was added dropwise in a THF solution (5 ml) of 4-carboxy benzaldehyde (500 mg, 2.97 mmol). The mixture was refluxed until the HCl evolution ceased. The mixture was cooled to room temperature and concentrated under reduced pressure to give the acid chloride as a colourless solid. This solid, dissolved in THF (5 ml), was added dropwise at 0° C. to an ethereal solution of 1-azido 3-aminopropane (300 mg, 2.97 mmol) and triethylamine (500 μl, 3.56 mmol). The mixture was then stirred at room temperature for 1 hour and washed with a saturated solution of $NaHCO_3$ (15 ml). The aqueous layer was extracted with $CHCl_3$ (10 ml×2) and the organic layers combined, dried over sodium sulfate, filtered and concentrated under reduced pressure. The residue was chromatographed with ethyl acetate-petroleum ether (2:1) ($R_f$ 0.42) to give compound 6 as a pale yellow oil (550 mg, 80%); $v_{max}(CHCl_3)/cm^{-1}$ 3400 (NH), 2980–2800 (CH), 2101 (—$N_3$), 1700 (CO aldehyde), 1680 (CO amide), 1520 (C=$C_{ar}$); $δ_H$(500 MHz; $CDCl_3$) 1.91 (2H, m, —$CH_2$—), 3.43 (2H, t, J 6.48, $CH_2N_3$), 3.55 (2H, td, J 6.53 and 6.13, $CH_2$ NH), 6.91 (1H, s broad, NH), 7.89 (2H, d, J 8.80, $H_{ar}$), 7.91 (2H, d, J 8.80, $H_{ar}$), 10.04 (1H, s, CHO); $δ_C$(125.78 MHz; $CDCl_3$) 28.53 (—$CH_2$—), 37.97 ($CH_2N_3$), 49.47 ($CH_2NH$), 127.57, 129.71 (4 $CH_{ar}$) 138.09, 139.52 (2 $C_{ar}$), 166.59 (CONH), 191.50 (CHO);m/z (CI) 233 [$MH^+$, 100%], 205 [$(M-N_2)^+$, 13], 133 [($OHC-Ph-CO^+$), 18]; HRMS: Calc. for $C_{11}H_{12}N_4O_2$: 232.2276. Found: 233.1039 ($MH^+$).

N-[α-benzotriazol-1-yl-para-allylbenzoate]-phenylacetamide7.—A mixture of phenylacetamide (1.73 g, 12.8 mmol), benzotriazole (1.52 g, 12.8 mmol) and compound 5 (2.43 g, 12.8 mmol), was refluxed in toluene (15 ml), for 48 hours. The solvent was evaporated under reduced pressure and the residue was purified by chromatography with ethyl acetate-petroleum ether (1:1) to give 7 as a white solid (3.2 g, 62%): $R_f$ 0.43; $δ_H$(500 MHz; $CDCl_3$) 3.60 (1H, d, J 15.40, $PhCH^a$), 3.62 (1H, d, J 15.40, $PhCH^b$), 4.78 (2H, d, J5.70, COO—$CH_2$), 5.27 (1H, dd, J 10.50 and 1.41, —CH=$CHH_{cis}$). 5.37 (1H, dd, J 17.20 and 1.41, —CH=CHHtrans). 5.98 (1H, ddt, J 17.20, 10.00 and, 5.70, —CH=CHH), 7.17–7.24 (5H, m, Ph $CH_2$), 7.23 (2H, d, J 8.40, $C_6H_4$), 7.36 (1H, dd, J 7.20, 7.60, benzotriazole), 7.43 (1H, dd, J 7.20, 7.60, benzotriazole), 7.59 (1H, d, J 9.00, NHCH), 7.90 (2H, d, J 8.40, $C_6H_4$), 7.96 (1H, d, J 8.75, benzotriazole), 8.05 (1H, d, J 8.75, benzotriazole), 8.14 (1H, d, J 9.00, NHCH); $δ_C$(125.78 MHz; $CDCl_3$) 42.84 ($PhCH_2$), 63.90 (NHCH), 65.64 (COO—$CH_2$), 109.70 (—CH=$CH_2$), 118.34 (—CH=$CH_2$), 119.77, 124.45, 126.44, 127.33, 128.04, 128.80, 129.11, 130.05, 130.71 (13 $CH_{ar}$), 131.81, 132.64, 133.85, 140.70, 145.47 (5 C), 165.25 ($CO_2$allyl), 171.11 (CONH); m/z (CI) 308 [$(M-C_6H_4N_3)^+$, 100%], 216 [$(M-C_6H_4N_3-PhCH_2)^+$, 28], 120 ($C_6H_6N_3^+$, 60), 91 ($PhCH_2^+$, 10).

N-[α-benzotriazol-1-yl-N'-azidopropyl benzamide]-phenylacetamide 8.—A mixture of phenylacetamide (585 mg, 4.31 mmol), benzotriazole (515 mg, 4.31 mmol) and compound 6 (1 g, 4.31 mmol) was refluxed in toluene (15 ml) for 12 Hours. The solvent was removed in vacuo, the residue washed with diethylether (10 ml×2) and chromatographed with ethyl acetate-petroleum ether (2:1) ($R_f$ 0.34) to give compound 8 as a white crystalline solid (1.05 g, 52%), m.p. 146° C.; $v_{max}(CHCl_3)/cm^{-1}$ 3400 (NH), 2980–2800 (CH), 2101 (—$N_3$), 1674 (CO), 1521 (C=$C_{ar}$); $δ_H$(500 MHz; $CD_3OD$) 1.87 (2H, m, —$CH_2$—), 3.39 (2H, t, J 6.65, $CH_2N_3$), 3.44 (2H, t, J 6.85, $NHCH_2$ ), 3.64 (1H, d, J 14.3, $PhCH^a$), 3.67 (1H, d, J 14.3, $PhCH^b$), 7.24 (5H, m, $C_6H_5$), 7.38–7.51 (4H, m, benzotriazole), 7.69 (1H, d, J 8.35, NHCH), 7.83 (2H, d, J 8.00, $C_6H_4$), 8.02 (2H, d, J 8.00, $C_6H_4$); $\delta_H$(500 MHz; $CDCl_3$) 6.90 (1H, s broad, $NHCH_2$), 8.15 (1H, d, J 9.00, NH CH); $\delta_C$(125–78 MHz; $CD_3OD$) 29.72 (—$CH_2$—), 38.48 ($CH_2N_3$), 43.22 ($PhCH_2$), 50.24 ($NHCH_2$), 66.74 (NHCH), 111.77, 120.22, 125.96, (CH benzotriazole), 128.03, 128.90, 129.15, 129.55, 130.08 ($CH_{ar}$), 133.73, 136.21, 136.54, 140.58, 146.84 ($C_{ar}$), 169.47 ($CONHCH_2$), 174.01 (BzCONH); m/z ($ES^+$) 469.60 [$MH^+$, 100%], 491.60 [$MNa^+$, 48], 133 [$MK^+$, 24].

N-[α-thioethyl-p-allylbenzoate]-phenylacetamide 9.—A solution of compound 7 (2.30 g, 5.40 mmol) and technical grade ethylthiolate sodium salt (563 mg, 6.7 mmol) in THF (20 ml) was stirred at room temperature for 2 hours. Distilled water (35 ml) was added to the reaction mixture, the aqueous layer was extracted with $CHCl_3$ (20 ml×2) and the organic layers combined, dried over sodium sulfate, filtered and concentrated under reduced pressure. The residue was purified by chromatography with ethyl acetate-petroleum ether (1:1) to give compound 9 as a white solid (1.38 g, 70%), $R_F$ 0.52; $\delta_H$(500 MHz; $CDCl_3$) 1.24 (3H, t, J 7.40, $CH_3$ $CH_2S$), 2.43–2.50 (1H, m, $CH_3CH^aS$), 2.56–2.63 (1H, m, $CH_3CH^bS$), 3.64 (1H, d, J 15.70, $PhCH^a$), 3.65 (1H, d, J 15.70, $PhCH^b$), 4.79 (2H, d, J 2.54, $CO_2CH_2$—), 5.27 (1H, dd, J 9.60 and 2.20, —CH=$CHH_{cis}$). 5.40 (1H, dd, J 17.20 and 2.20, —CH=$CHH_{trans}$), 6.00 (1H, ddt, J 17.20, 9.60 and 2.54, —CH=CHH), 6.10 (1H, d, J 9.25, NHCH), 6.28 (1H, d, J 9.25, NHCH), 6.28 (1H, d J 9.25, NHCH), 7.25–7.45 (7H, m, Ar), 7.98 (2H, d, J 8.40, $C_6H_4$); $\delta_C$(125.78 MHz; $CDCl_3$) 14.65 ($CH_3CH_2$), 25.63 ($CH_3CH_2$), 43.71 ($PhCH_2$), 55.73 (NHCH), 65.56 ($CO_2H_2$), 109.58 (—CH=$CH_2$), 118.25 (CH=$CH_2$), 126.35, 127.63, 129.10, 129.17, 129.24, 129.97, 130.24 ($9CH_{ar}$), 132.08, 134.34, 144.08 ($3C_{ar}$), 165.66 ($CO_2$allyl), 170.21 (CONH); m/z (CI) 308 [$(M-SEt)^+$, 100%], 136 ($PhCH_2CONH_3^+$, 8), 120 ($PhCH_2CO^+ + H^+$, 18), 9($PhCH_2^+$, 12).

N-[α-thioethyl-N'-azidopropyl benzamide]-phenylacetamide 10.—A solution of compound 8 (100 mg, 0.214 mmol) and technical grade ethylthiolate sodium salt (39 mg, 0.4 mmol) in THF (3 ml) was stirred at room temperature for 1 hour. Distilled water (15 ml) was added to the reaction mixture, the aqueous layer was extracted with $CHCl_3$ (10 ml×2) and the organic layers combined, dried over sodium sulfate, filtered and concentrated under reduced pressure to give compound 10 as a white solid (85 mg, 97%), m.p. 142° C.; $\nu$max($CHCl_3$)/$cm^{-1}$ 3400 (NH), 2980–2800 (CH), 2101 (—N=N=N), 1671 (CO), 1520 (C=$C_{ar}$); $\delta_H$(500 MHz; $CDCl_3$) 1.25 (3H t,J 7.4, $CH_3$ $CH_2S$), 1.90 (2H, m, —$CH_2$—), 2.45–2.51 (1H, m, $CH_3CH^aS$), 2.57–2.62 (1H, m, $CH_3CH^bS$), 3.44 (2H, t, J 6.50, $CH_2N_3$), 3.54 (2H, td, J 6.4 and 5.65, $NHCH_2$ ), 3.64 (1H, d, J 15.75, $PhCH^a$), 3.66 (1H, d, J 15.75, $PhCh^b$), 6.00 (1H, d, J 9.20, CHNH), 6.26 (1H, d, J 9.20, CHNH), 6.39 (1H, t, J 5.65, $NHCH_2$), 7.27–7.37 (5H, m, $H_{ar}$), 7.38 (2H,d,J 8.30, $C_6H_4$), 7.69 (2H, d, J 8.30, $C_6H_4$); $\delta_C$(125.78 MHz; $CD_3OD$) 14.98 ($CH_3$), 26.27 ($CH_2S$), 29.78 (—$CH_2$—), 38.45 ($CH_2N_3$), 43.70 ($PhCH_2$), 50.27 ($NHCH_2$), 56.57 (NHCH), 127.96, 128.51, 129.57, 130.04, 130.14 ($CH_{ar}$), 135.23, 136.90, 144.54 ($C_{ar}$), 169.86 ($CONHCH_2$), 173.40 (BzCONH); m/z (CI) 412 [$MH^+$, 70%], 384 [$(M-N_2)^+$, 73], 136 ($BzCONH_3^+$, 100), 120 ($BzCO^+$, 80), 91 ($PhCH_2^+$, 40).

N-[α-(6-O-1,2,3,4-tetra-O-acetyl-β-D-glucopyranose)-p-allylbenzoate]-phenylacetamide 11.—A solution of compound 9 (500 mg, 1.22 mmol) and 1,2,3,4-tetra-O-acetyl-β-D-glucopyranose (440 mg, 1.22 mmol) in dry dichloromethane (30 ml) was stirred with molecular sieve powder 4 Å (1 g) for 15 minutes at room temperature, then for 15 minutes at 0° C. N-iodosuccinimide (425 mg, 1.83 mmol), previously dried at high vacuum, was then added to the mixture which changed instantaneously to a dark purple colour. The reaction mixture was stirred at 0° C. for 30 minutes, washed with a saturated solution of $NaHCO_3$ (70 ml) containing sodium thiosulfate. The aqueous layer was extracted with $CHCl_3$ (50 ml×2) and the organic layers combined, dried over sodium sulfate, filtered and concentrated under reduced pressure. The residue was purified by chromatography with ethyl acetate-petroleum ether (2:1) to give compound 11(2 diastereoisomers) as a white solid (433 mg, 52%), $R_f$ 0.5; $\delta_H$(500 MHz; $CDCl_3$) 1.94, 1.95, 1.99, 2.01, 2.02, 2.06, 2.07 (24H, 7s, 8 $CH_3CO$, 2 diast. 3.57 (2H, s, $PhCH_2$, 1 diast.), 3.63 (2H, s, $PhCH_2$, 1 diast.), 3.69–3.83 (6-H 5-H, 2 diast.), 4.79 (4H, dm, J 5.62, $CO_2CH_2$—, 2 diast.), 5.06–5.11 (2H, m, 2-H, 2 diast. 5.14–5.25 (4H, m, 3-H and 4-H, 2 diast.), 5.32 (2H, dd, J 10.43 and 1.43, —CH=CHH 2 diast.), 5.40 (2H, dd, J 14.50 and 1.43, —CH=$CHH_{trans}$, 2diast.), 5.65 (1H, d, J 8.20, 1-H, 1 diast.), 5.69 (1H, d, J 8.26, 1-H, 1 diast.), 6.00 (2H, m, CH=$CH_2$, 2 diast.), 6.14 ( d, J 9.5, NH, 1 diast.), 6.21 (1H, d, J 9.70, NH, 1 diast.), 6.22 (1H, d, J 9.50, NHCH, 1 diast.), 6.24 (1H, d, J 9.70, NHCH, 1 diast.), 7.30 (14H, m, Ph, 2 diast.), 7.97 (2H, d, J 8.40, $C_6H_4$, 1 diast.), 7.98 (2H, d, J 8.40, $C_6H_4$, 1 diast.); $\delta_C$(125.78 MHz; 20.52, 20.69 ($CH_3CO$—, 2 diast.), 43.55, 43.72 ($PhCH_2$, 2 diast.), 65.50 ($CO_2CH_2$), 66.2 66.64 (6-C, 2 diast.), 68.18, 68.37, 70.25, 72.85, 73.31, 73.47, 79.74, 80.06 (2-C, 3-C, 4-C, 5-C and CHNH, 2 diast.), 91.67 (1-C), 118.19 (—CH=$CH_2$), 132.04 (CH=$CH_2$), 125.89, 127.40, 127.50, 128.94, 129.03, 129.08, 129.18, 129.67, 129.76 ($CH_{ar}$), 134.13, 143.37, 143.62 ($C_{ar}$), 165.71 ($CO_2$allyl), 168.90, 169.17, 169.41, 169.47, 170.00 ($CH_3CO$), 171.19, 171.32 (CONH, 2 diast.); m/z (CI) 366 [(tetra-O-acetyl glucopyranoside$^+ + NH_4^+$), 22%], 308[(M-tetra-O-acetyl glucopyranoside)$^+$, 83], 289 (tetra-O-acetyl glucopyranoside$^+$−10Ac, 100), 229 (tetra-O-acetyl glucopyranoside$^+$−20Ac, 26), 91 ($PhCH_2^+$, 29).

N-[α-(6-O-αβD-glucopyranose)-p-allylbenzoate]-phenylacetamide 13.—A solution of compound 11 (100 mg, 152.7 μmol) in methanol (2.6 ml) containing $Et_3N$ (260 μg) was stirred at room temperature for 18 hours. The reaction mixture was reduced in volume and the product was recrystallised in a mixture of $CHCl_3$ (2 ml) and $Et_2O$ (3 ml). The white solid was collected by filtration and dried in vacuo (69 mg, 92%) to give 13 as a mixture of 4 diastereoisomers: $R_f$ 0.31 (MeOH/$CHCl_3$ 2:8); $\delta_H$(500 MHz; $CD_3OD$) 3.11–3.15 (2H, m, 2-H, 2 diast.), 3.32–3.38 (8H, m, 2-H, 3-H, 2 diast. and 4-H, 4 diast.), 3.42–3.45 (2H, m, 5-H, 2 diast.), 3.59 (8H, 2 s, $PhCH_2$, 4 diast.), 3.65–3.98 (8H, m, 6-H, 4-H, 3-H, 2 diast.), 4.47 (2H, d, J 7.80, 1-$H_α$, 2 diast.), 5.08 (2H, d, J 6.00, 1-$H_β$, 2 diast.), 5.28 (2H, dd, J diast.) 10.50 and 1.30, $OCH_2CH$=$CHH_{cis}$, 2 diast.), 5.40 (2H, dd, J 1.5, 17.2, $OCH_2CH$=$CHH_{trans}$, 2 diast.), 6.02–6.10 (2H, m, CH=$CH_2$, 2 diast.), 6.25–6.28 (2H, m, NHCH, 2 diast.), 7.22–7.25 (4H, m, $PhCH_2$, 2 diast.), 7.30–7.32 (6H, m, Ph $CH_2$, 2 diast.), 7.54 (4H, d, J 8.20, $C_6H_4$, 2 diast.), 8.00 (4H, dd, J 8.40, 2.60, $C_6H_4$, 2 diast.); $\delta_C$(125.78 MHz; $CDCl_3$) 43.87 ($PhCH_2$), 66.67 ($CH_2CH_2$), 68.79, 69.05, 69.20 (6-C, 2 diast.), 71.69, 72.00, 72.07, 72.98, 73.83, 74.90, 76.28, 76.62, 76.81, 78.13, 81.75 (2-C, 3-C, 4-C, 5-C and CHNH, 2 diast.), 94.01 (1-$C_α$), 98.25 (1-$C_β$), 118.52 (—CH=$CH_2$), 127.60, 127.98, 128.15, 129.61, 130.52, 131.10, 131.19 ($CH_{ar}$ and CH=$CH_2$), 133.66, 136.70, 146.16 ($C_{ar}$), 167.33 ($CH_2$allyl), 174.42 (CONH); m/z (CI) 488 ($MH^+$, 40%), 308 [(M-glucopyranoside)$^+$, 100], 136 [($PhCH_2CONH_3^+$), 61], 119 [($PhCH_2CO^+$), 60], 91 ($PhCH_2^+$, 68)

N-[α-(6-O-α,β-D-glucopyranose)-p-benzoic acid morpholine salt]phenylacetamide 4.—A solution of compound 13 (58 mg, 119 μmol), $Pd(PPh_3)_4$ (13.8 mg, 11.9 μmol) and morpholine (51.9 μl, 595 μmol) in THF (1 ml) was stirred at room temperature for 2.5 hours. The reaction mixture was concentrated under reduced pressure, the residue was diluted with water (10 ml) and the solvent was removed to give compound 4 (mixture of 4 diastereoisomers) as a pale yellow solid (47 mg, 71%), $R_f$ 0.25 (MeOH/$CHCl_3$/$H_2O$ 4:5:1); $\delta_H$(500 MHz; $CD_3OD$) 3.05–3.07[16H, m, $CH_2OCH_2$ (morpholine), 4 diast.], 3.12–3.16 (2H, m, 2-H, 2 diast.), 3.29–3.39 (8H, m, 2-H, 3-H, 2 diast. and 4-H, 4 diast.), 3.41–3.44 (2H, m, 5-H, 2 diast.), 3.59 (8H, s, PhCH$_2$, 4 diast.), 3.63–3.97[28H, m, CH$_2$NCH$_2$ (morpholine), 6-H$^a$, 6-H$^b$, 4 diast. and 5-H, 3-H, 2 diast.), 4.46 (2H, 2 d, J 7.8 and 7.8, 1-H$_\beta$, 2 diast.), 5.08–5.10 (2H, m, 1-H$_\alpha$, 2 diast.), 6.22–6.25 (4H, m, NHCH 4 diast.), 7.21–7.25 (4H, m, Ph, pH, 4 diast.), 7.30–7.32 (16H, m, Ph, 4 diast.), 7.45 (4H, d, J 8.2, C$_6$H$_4$, m-H, 4 diast.), 7.93 (8H, dd, J 8.3, 2.7, C$_6$H$_4$, o-H, 4 diast.); $\delta_C$(125.78 MHz; CD$_3$OD) 43.84 (PhCH$_2$), 44.90, 65.50 (CH$_2$ morpholine), 68.64, 68.92, 69.35 (6-C), 70.18, 71.70, 72.03, 73.81, 74.85, 76.26, 76.81, 78.13, 78.73, 79.36 (2-C, 3-C, 4-C, 5-C), 82.03 (CHNH), 93.98 (1-C$_{\alpha_2}$), 98.23 (1-C$_\beta$), 126.96, 127.94, 129.59, 130.17 (CH$_{ar}$, 130.38, 136.77, 143.50 (C$_{ar}$), 159.18 (CO$_2$—), 171.72 (CONH); m/z (ES$^-$) 446.53 (M-H-, 100%).

N-[α-(6-O-α,β-D-glucopyranose)-N'-azidopropyl benzamide]-phenylacetamide 14.—A solution of compound 10 (50 mg, 0.122 mmol) and 1,2,3,4-tetra-O-acetyl-β-D-glucopyranose (42 mg, 0.122 mmol) in dry dichloromethane (3 ml) was stirred with molecular sieve powder 4 Å (100 mg) for 15 minutes at room temperature followed by 15 minutes at 0° C. N-iodosuccinimide (41 mg, 0.183 mmol), previously dried at highvacuum, was then added to the mixture which changed instantaneously to a dark purple colour. The reaction mixture was stirred at 0° C. for 30 minutes, washed with a saturated solution of NaHCO$_3$ (10 ml) containing sodium thiosulfate. The aqueous layer was extracted with CHCl$_3$ (10 ml×2) and the organic layers combined, dried over sodium sulfate, filtered and concentrated under reduced pressure. The residue was dissolved in methanol (1.3 ml) and triethylamine (130 µl) was added dropwise. The reaction mixture was then stirred at room temperature overnight, and the solution was evaporated. The residue was precipitated with diethylether (4 ml) to give a white solid which is dissolved in methanol (200 µl) and loaded on a reverse-phase column (1.5×46 cm; packed in methanol and washed with methanol-water AnalR 60:40).

The compound was eluted with methanol-water (60:40) for 20 minutes and then with methanol-water (50:50). The fractions containing 14 were concentrated under reduced pressure to give compound 14 (2 apparent diastereoisomers) as an pale yellow oil (20 mg, 32%); $v_{max}$ (CHCl$_3$)/cm$^{-1}$ 3400 (NH), 2980–2800 (CH), 2101 (N$_3$), 1663 (CO), 1520 (C=C$_{ar}$); $\delta_H$(500 MHz; CD$_3$OD) 1.88 (4H, m, —CH$_2$—), 3.15 (1H, m, 2-H, diast. A), 3.35 (1H, m, 2-H, diast. B), 3.40 (4H, t, J 6.70, CH$_2$N$_3$), 3.45 (4H, t, J 6.90, NHCH$_2$ ), 3.59 (4H, s, PhCH$_2$), 3.65–4.00 (6H, m, 6-H and 5-H), 4.47 (1H, dd, J 7.78 and 1.96, 1-H$_\alpha$, diast. A), 5.09 (1H, dd, J 5.78 and 3.67, 1-H$_\beta$, diast. B), 6.25 (1H, d, J 2.25, CHNH, 1 diast.), 6.26 (1H, d, J 2.25, CHNH, 1 diast.), 7.24 (2H, m, Ph CH$_2$), 7.30 (8H, m, PhCH$_2$), 7.51 (4H, d, J 8.21, C$_6$H$_4$), 7.79 (4H, dd, J 8.39 and 2.25, C$_6$H$_4$); $\delta_C$(125.78 MHz; CD$_3$OD) 29.77 (—CH$_2$—), 38.45 (CH$_2$N$_3$), 43.87 (PhCH$_2$), 50.27 (NHCH$_2$), 68.73, 68.97, 69.13 (6-C), 71.69, 71.99, 73.84, 74.90, 76.28, 76.64, 76.80, 78.13, 81.79 (5 CH), 94.01 (1-C$_\alpha$), 98.26 (1-C$_\beta$), 127.50, 127.97, 128.27, 129.60 (9 CH$_{ar}$), 130.16, 135.46, 136.73 (3 C$_{ar}$), 169.94 (CONHCH$_2$), 174.40 (BzCONH).

Glycosyl serine derivative 16.—To a stirred solution of 9 (0.05 g, 0.127 mmol) in dichloromethane (1.5 cm$^3$) at 0° C. under an inert atmosphere was added 4A molecular sieve powder (0.1 g), followed by a solution of the suitably protected glycosyl serine (0.068 g, 0.127 mmol) in dichloromethane (1.5 cm$^3$). The mixture was stirred for 5 minutes, then N-iodosuccinimide (0.043 g, 0.19 mmol) was added upon which the reaction mixture turned a dark red-brown colour. After stirring for 15 minutes, thin layer chromatography (1:1, ethyl acetate: hexane) revealed no further change and the reaction mixture was filtered and diluted with chloroform (10 cm$^3$). The organic solution was washed with water (10 cm$^3$) and aqueous sodium thiosulfate (15 cm$^3$) and the aqueous extracts were back-extracted with chloroform (10 cm$^3$). The combined organic extracts were dried over sodium sulfate, filtered and concentrated in vacuo to yield a dark yellow oil. Purification by flash column chromatography eluting 40% ethylacetate/hexane gave the desired product 16 as a pale foam (0.0418 g, 0.05 mmol, 39%). $^1$H nmr (400 MHz; CDCl$_3$) $\delta_H$ (ppm) 7.82 (2H, d, aromatic), 7.65 (4H, m, arH, HC, aromatic), 7.24 (7H, m, aromatic), 6.05 (1.4H, allylic H), 6.05 (1H, m, allylic CH), 5.75 (2H, m, H$_c$, H$_k$), 5.40 (1.5H, 0.5H=H$_A$, 1H=terminal allylic), 5.28 (1.5H, 0.5H=H$_A$, 1H=terminal allylic), 5.12 (1H, dd, H$_D$), 4.84 (2H, d, allylic CH$_2$), 4.26 (2H, m, H$_B$ and H$_F$), 4.15 (1H, m, H$_G$) 4.04 (0.5H, m., H$_H$), 3.96 (0.5H, m, H$_H$), 3.82 (0.5H, m, H$_I$), 3.78 (0.5H, m, H$_I$), 3.66 (0.5H, m, H$_1$), 3.58 (2H, s, benzylic CHO, 3.44 (3H, s, CH$_3$), 2.08 (3H, d, CH$_3$), 2.03 (3H, d, CH$_3$), 1.84 (3H, d, CH$_3$). The proton spectrum is "missing" 2 NH's which are believed to be obscured by the aromatic proton signals. The spectrum shows that the compound is an approx 1:1 ratio of diastereomers; $^{13}$C nmr (100 MHz; CDCl$_3$) $\delta_C$ (ppm) 173.0, 172.0, 170.8, 170.7, 170.6, 170.1, 170.0, 169.5, 169.4, 165.8 (10×C=O), 145.2, 145.0 (2×C), 144.9, 134.4, 134.2, 132.2 (4×CH), 132.1, 131.3 (2×C), 131.2, 130.1, 130.0, 129.9, 129.8, 129.2, 129.1, 129.0, 127.5, 127.4, 126.2, 126.1, 123.53×CH), 118.4, 118.3 (terminal allylic CH$_2$), 98.1, 97.7 (2×CH anomeric), 72.0, 71.9 (2×CH), 70.5 (CH), 70.1, 70.0 (2×CH$_2$), 68.9, 68.8 (2×CH), 65.6 (CH$_2$), 65.5, 65.3 (2×CH$_2$), 61.9, 61.8 (2×CH), 58.3, 57.5 (2×CH), 54.4, 54 (2×CH), 52.3, 52.2 (CH$_3$), 43.8, 43.7 (2×CH$_2$, 29.7 (CH$_2$), 20.7, 20.7, 20.6, 20.4 (CH$_3$); m/z (EI) found 843

N-[4-azido-1-(benzotriazol-1'-yl)butyl]phenylacetamide 20.—4-bromobutanal (3.34 g, 0.022 g), benzotriazole (2.63 g, 0.022 mol) and phenylacetamide (2.99 g, 0.022 mol) were dissolved in dry toluene (190 ml) in a Dean-Stark apparatus under nitrogen and heated under reflux for 2 hours. The toluene solution was cooled to room temperature and then washed with saturated sodium carbonate solution (70 ml×3). Each wash was back-extracted with toluene (50 ml). The combined organics were dried (MgSO$_4$) and the solvent was removed in vacuo. The product was purified by column chromatography [silica, petroleum ether: ethyl acetate (2:1)] to give a white solid (52% 4.77 g). mp 109.6–110° C.; R$_f$ 0.45 [petroleum ether: ethyl acetate (1:1)]; $\delta_H$ (CDCl$_3$; 250 MHz) 1.76 (2H, m, CH$_2$CH$_2$Br), 2.48 (2H, m, CHCH$_2$), 3.34 (m, 2H, CH$_2$Br), 3.52 (1H, d, J 16.0, PhCH$_2$), 3.58 (1H, d, J 16.0, PhCH$_2$), 6.59 (1H, d, J 9.42, NH), 6.71 (1H, m, CH), 7.59 (9H, m, CH$_{ar}$); $\delta_C$ (CDCl$_3$; 63 MHz) 28.19 (1C, CH$_2$CH$_2$Br), 32.03, 32.35, (2C, CH$_2$CH$_2$CH$_2$), 42.97 (1C, PhCH$_1$), 61.22 (1C, CH), 110.17–109.03 (9H, 7 signals, CH$_{ar}$), 132.64, 133.76, 145.28 (3C, C$_{ar}$), 171.09 (1C, CO); m/z 389 (56.4%, MH$^+$), 269 (100%, [M-benzotriazole]$^+$), 120 (97.9%, [PhCH$_2$CO]$^+$); (Found: MH$^+$, 387.0813. C$_{18}$H$_{19}$BrN$_4$O requires MH$^+$, 387.8205; $v_{max}$ (CHCl$_3$)/cm$^{-1}$ 1685 (C=O).

A mixture of this bromide (1.00 g, 2.58 mmol) and sodium azide (0.34 g, 5.23 mmol) in DMF (4 ml) was stirred at room temperature for 5 hours. Chloroform (30 ml) and distilled water were added. The mixture was separated and the aqueous extracted with chloroform (10 ml). The combined organics were washed with saturated ammonium chloride solution (30 ml×3), distilled water (30 ml), dried over MgSO$_4$ and concentrated in vacuo. The product was purified by column chromatography (silica, petroleum ether-:ethyl acetate (1:1) to give a white solid (82%, 0.74 g). R$_f$ 0.42 [ethyl acetate: petroleum ether (1:1)]; $\delta_H$ (CDCl$_3$; 200 MHz) 1.46 (2H, m, CHCH$_2$), 2.41 (2H, m, CH$_2$CH$_2$CH$_2$), 3.28 (2H, m, CH$_2$N$_3$), 3.50 (2H, d, J 2.20, PhCH$_2$), 6.69 (2H, m, CH, NH), 7.07–7.98 (9H, m, CH$_{ar}$); $\delta_c$ (CDCl$_3$; 63MHz), (1C, CH$_2$CH$_2$CH$_2$), 30.98 (9C, CH$_2$CH$_2$CH$_2$N$_3$), 42.90 (1C, PhCH$_2$), 50.30 (1C, CH$_2$N$_3$), 61.55 (1C, CH), 110.22–128.99 (9C, CH$_{ar}$), 132.67, 133.83, 145.18 (3C, $C_{ar}$); m/z 351 (30.1%, MH⁺), 232 (10.5%, [M-benzotriazole]⁺), 204 (19.4%, [322-N₂]⁺); (Found: MH⁺, 350.1721. $C_{18}H_{19}N_7O$ requires MH⁺, 350.1729); $v_{max}$ (CHCl₃)/cm⁻¹ 1682 (C=O), 2102 (N₃).

N-[4-azido-1-(ethylsulfanyl)butyl] phenylacetamide21.—A mixture of N-[1-benzotriazole-1'-yl)-4-azidobutyl]phenylacetamide (20) (0.300 g, 0.859 mmol) and technical grade ethylthiolate sodium salt (0.140 g, 1.66 mmol) in dry THF (15 ml) was stirred at room temperature under nitrogen for 2.5 hours. Chloroform (50 ml) and distilled water (30 ml) were added. The mixture was separated and the aqueous extracted with chloroform (10 ml). The organic layer was washed with water (50 ml×2) each time back-extracting the aqueous with chloroform (20 ml). The combined organics were dried (MgSO₄) and the solvent removed by distillation in vacuo. The product was purified by column chromatography [silica, petroleum ether: ethyl acetate (2:1)] to give a pale yellow solid (67%, 0.167 g). $R_f$ 0.48 [ethyl acetate: petroleum ether (1:2)]; $\delta_H$ (CDCl₃; 200 MHz) 1.13 (3H, t, J 7.5, SCH₂CH₃), 1.56 (4H, m, CH₂CH₂CH₂N₃), 2.40 (2H, m, SCH₂), 3.19 (2H, t, J 6.2 CH₂N₃), 3.53 (2H, s, PhCH₂), 5.09 (1H, m, NHCH), 5.36 (1H, d, J 9.2, NH), 7.26 (5H, m, CH$_{ar}$); $\delta_c$ (CDCl₃; 63MHz) 14.77 (1C, CH₃), 24.57 (1C, CH₂CH₂CH₂) 25.52 (1C, SCH₂), 32.97 (1C, CH₂CH₂CH₂N₃), 43.75 (1C, PhCH₂), 50.57 (1C, CH₂N₃), 53.02 (1C, CH), 127.47–129.13 (5C, CH$_{ar}$), 134.33 (1C, C$_{ar}$); m/z 293 (3.4%, MH⁺), 250 (13.5%, [M-N₃]⁺), 231 (35.8%, [M-SEt]⁺); (Found: MH⁺293.1442. $C_{14}H_{20}N_4OS$ requires MH⁺293.1436); $v_{max}$ (CHCl₃)/cm⁻¹ 1668 (C=O), 2099 (N₃).

N-[4-amino-1-(ethylsulfanyl)butyl]-phenylacetamide 22.—A mixture of N-[4-azido-1-(ethylsulfanyl) butyl] phenylacetamide (21) (0.130 g, 0.45 mmol), triphenylphosphine (0.140 g, 0.54 mmol) and distilled water (0.1 ml) in THF (5 ml) was stirred at room temperature overnight. The solvent was removed in vacuo and the material purified by column chromatography [silica, DCM: methanol (9:1)] to give an oil (0.118 g. 74%). $R_f$ 0.00 [petroleum ether: ethyl acetate (1:1)]; $\delta_H$ (CDCl₃; 250 MHz). 1.18 (3H, t, J 7.4 CH₃), 1.61 (4H, m, CH₂CH₂CH), 2.47 (2H, m, SCH₂), 2.71 (4H, m, CH₂NH₂), 3.59 (2H, s, PhCH₂), 5.16 (1H, dt, J 9.6, J 6.4, CH), 6.25 (1H, d, J 9.7, NH), 7.31 (5H, m, CH$_{ar}$).

1-O-(methyl-2(R)-N-(benzyloxycarbonyl)-propanoate)-2-deoxy-2-acetamido-β-D-glucopyranoside 23.—$\delta_H$ (600 MHz; d₆-DMSO) 7.65 (1H, d, J 8.7, NHAc), 7.35 (6H, m, 5 aromatic H+NHZ), 5.01 (2H, s, CH₂Ph), 4.99 (1H, br.s, OH), 4.92 (1H, br.s, OH), 4.50 (1H, br.s, OH), 4.31 (1H, d, J 8.4, 1-H), 4.27 (1H, m, CHNHZ), 3.92 (1H, m), 3.67 (2H, m), 3.63 (3H, s, CO₂CH₃), 3.57 (1H, br.s), 3.44 (1H, m), 3.33 (3H, m), 3.26 (1H, m), 1.78 (3H, s, NHCOCH₃); $\delta_c$ (90 MHz; d₆-DMSO) 170.68 (C, CHCO₂CH₃), 169.57 (C, NHCO₂CH₂Ph), 155.95 (C, NHCOCH₃), 136.82 (C, aromatic), 128.42 (CH, aromatic), 127.82 (CH, aromatic), 101.17 (CH, C-1 anomeric), 77.21 (CH), 74.15, 70.15 (3×CH), 67.57 (OCH₂Ph), 65.77 (OCH₂CHNHZ), 61.07 (CH₂, C-6), 55.18, 54.12 (2×CH), 52.12 (CH₃, CO₂CH₃), 22.99 (CH₃, NHCOCH₃); m/z (FAB) Found 457.18315 (M⁺+H), $C_{20}H_{29}N_2O_{10}$ requires 457.18222.

N-benzyloxycarbonyl-O-[O-(2,3,4,6-tetra-O-acetyl-β-D-galactopyranosyl)-(1-4)-3, 6-di-O-acetyl-2-acetamido-deoxy-β-D-glucopyranosyl]-L-serine methyl ester 24.—To a suspension of the acceptor 23 (10 mg, 22 μmol) in 100 mM sodium cacodylate buffer, pH 7.4, (480 μl) was added a solution of sodium azide (40 mM, 80 μl) and manganese chloride (50 mM, 33 μl) and the mixture was sonicated for 20 minutes. To this was added CIAP (4.9 μl, 4.9U), BSA (29.4 μl, 0.59 mg), UDP-glucose (22 mg, 351 μmol), UDP-glucose epimerase (133 μl, 1.27 U) and β-1,4-galactosyl transferase (30.1 μl, 289 mU). The mixture was placed in a shaker and shaken at 37° C. for 48 hours, then transferred to two Eppendorf tubes and centrifugated for 5 minutes at 6500 rpm. The pellet was washed with 50% methanol-water and centrifugated again. The combined supernatant was transferred to a flask and freeze-dried to give a white solid, which was treated with acetic anhydride (0.5 ml) and pyridine (0.5 ml). The mixture was stirred at room temperature for 24 hours, then poured onto iced water (1 ml) and extracted with chloroform (3×3 ml). The combined organic layers were washed with 5% hydrochloric acid (2.5 ml), saturated sodium bicarbonate (2.5 ml), saturated brine (2.5 ml) and water (2.5 ml), then dried over sodium sulfate, filtered and concentrated in vacuo. The residue was purified by flash chromatography (methanol-dichloromethane). $\delta_H$(600 MHz, CDCl₃) 7.34 (5 H, m, Ph), 6.10 (1 H, d, J=9.2 Hz, NH), 5.80 (1 H, d, J=7.9 Hz, NH), 5.09 (2 H, s, CH₂-Ph), 5.06 (1 H, m), 4.86 (1 H, m), 4.49–4.42 (3 H, m) 4.31 (2 H, m), 4.19 (1 H, m), 4.11 (2 H, m), 3.97 (1 H, m), 3.83 (2 H, m) 3.72 (3 H, OCH₃), 3.69–3.56 (4 H, m), 2.08 (15 H, m, COCH₃), 2.03 (3 H, s, COCH₃), 1.87 (3 H, s, NHCOCH₃). $\delta_c$ (62.9 MHz, CDCl₃) 171.3–170.3 (C=O), 155 (1C, NHC=O), 136 (1 C, C-ipso), 128.4–128.2 (5 C, Ph), 100.8, 100.6 (2 C, C-1, C-1'), 77.1, 75.8, 73.3, 72.6, 72.2, 72.1 (6 C, CH), 68.4 (1 C, CH₂), 68.3 (1 C, CH), 67.0 (1 C, CH₂), 62.2 (2 C, CH₂), 54.0, 52.8 (2 C, CH), 52.6 (1 C, COOCH₃), 29.6, 22.9, 20.8, 20.7 (7 C, CH₃).

What is claimed is:

1. A method of synthesis of a material corresponding to the formula:

comprising a material corresponding to the following formula:

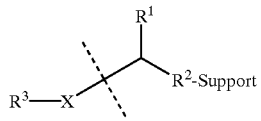

being cleaved as indicated enzymatically or non-enzymatically using acid catalysis in the presence of a nucleophile;

wherein

R¹ represents a group selected from the group consisting of —NH—CO—CH₂—Ph,

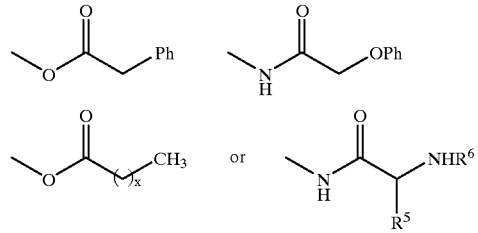

wherein x represents an integer; and

R⁵ and R⁶ each represents a non-interfering group;

R² represents an intermediate linked to a solid support selected from the group consisting of:

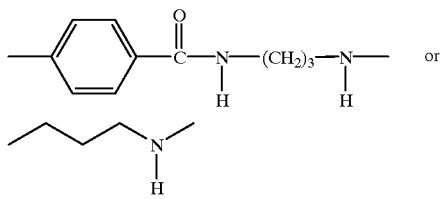

or

R³ represents an alkyl, a carbohydrate, (oligo-)saccharide, (glyco-)peptide, (glyco-)lipid, heterocycle or aromatic;

X represents O, N(H), N(R"), C(O)O, S, C(O)N(H) or C(O)N(R"), R" being a non-interfering group; and Support represents a solid support.

2. A method as claimed in claim 1 wherein R³ represents a residue of a (glyco-)peptide or (oligo-)saccharide.

3. A method as claimed in claim 1 wherein X represents O, N(H), N(R"), C(O)O, C(O)N(H) or S.

4. A method as claimed in claim 1 wherein Support represents an oxirane acrylic resin, or amilopropyl silica.

5. A method as claimed in claim 1 wherein the cleaving is performed by penicillin amidase.

6. The method as claimed in claim 1 wherein the material being cleaved is selected from the group consisting of:

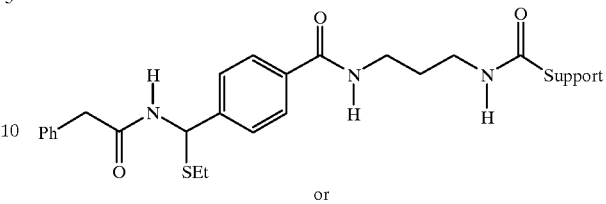

or

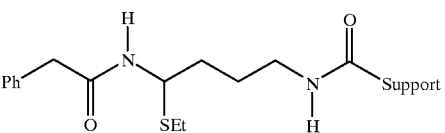

* * * * *